United States Patent [19]
Takahashi

[11] Patent Number: 6,095,971
[45] Date of Patent: Aug. 1, 2000

[54] ENDOSCOPE FLUID CONTROLLER

[75] Inventor: Kazuaki Takahashi, Omiya, Japan

[73] Assignee: Fuji Photo Optical Co., Ltd., Saitama, Japan

[21] Appl. No.: 09/175,315

[22] Filed: Oct. 20, 1998

[30] Foreign Application Priority Data

| Oct. 22, 1997 | [JP] | Japan | 9-308035 |
| Oct. 27, 1997 | [JP] | Japan | 9-311478 |
| Dec. 5, 1997 | [JP] | Japan | 9-352264 |
| Dec. 18, 1997 | [JP] | Japan | 9-364459 |

[51] Int. Cl.$^7$ .................................................. A61B 1/12
[52] U.S. Cl. .......................... 600/159; 600/11.8; 600/156
[58] Field of Search .................................. 600/118, 156, 600/158, 159

[56] References Cited

U.S. PATENT DOCUMENTS

| 4,402,310 | 9/1983 | Kimura | 600/158 |
| 4,982,726 | 1/1991 | Taira | 600/158 |
| 5,022,382 | 6/1991 | Ohshoji et al. | 600/156 |
| 5,125,909 | 6/1992 | Heimberger | 604/264 |
| 5,191,878 | 3/1993 | Iida et al. | 600/158 |
| 5,343,855 | 9/1994 | Iida et al. | 600/158 |
| 5,609,563 | 3/1997 | Suzuki et al. | 600/159 |
| 5,695,450 | 12/1997 | Yabe et al. | 600/156 |

OTHER PUBLICATIONS

Pat. Abstracts of Japan, Jap. Pat. Publ. No. 01297045A Nov. 30, 1989, Toshiba Corp Toshiba Med. Eng. Co. Ltd., Japan.
Pat. Abstracts of Japan, Jap. Pat. Publ. No. 01310638 Dec. 14, 1989, Toshiba Corp., Japan.

*Primary Examiner*—Linda C. M. Dvorak
*Assistant Examiner*—Brad C. Blaise
*Attorney, Agent, or Firm*—Snider & Associates; Ronald R. Snider

[57] ABSTRACT

An endoscope fluid controller of the present invention controls the opening/closing and flow rate of a duct. To control the flow rate of a water feed duct, air feed duct, and the like, for example, three pinch valves are disposed in series in a soft duct, and the pushing amount of a pressing portion of the pinch valve is adjusted so that the collapsing amount of soft duct changes. By controlling the opening/closing of the pinch valve by using a control switch disposed in the operation section, the flow rate in the duct can be controlled variably. In this case, three-stage control of flow rate can be carried out. In the case of a suction duct, the pinch valve can be disposed on the atmosphere open duct side. Also, a display section indicating the operation state and flow rate of each of various ducts is provided on a control panel etc. of an electromagnetic valve unit. On the soft duct other than the valve portion, a hard covering member for preventing duct deformation is disposed. Further, separately from the control switch in the operation section, a second control switch having the same function is disposed in an auxiliary peration section on the electromagnetic valve unit side.

13 Claims, 11 Drawing Sheets

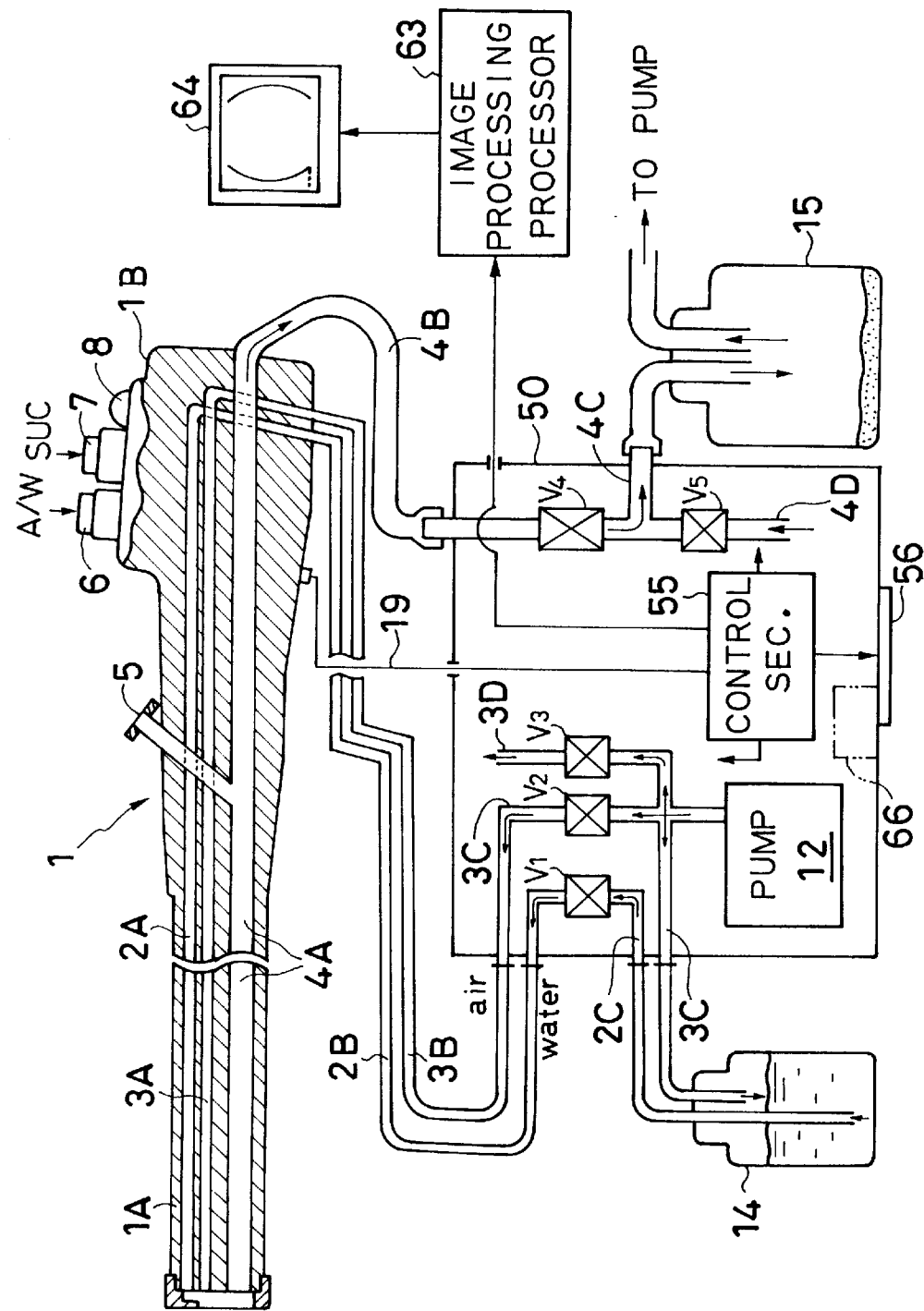

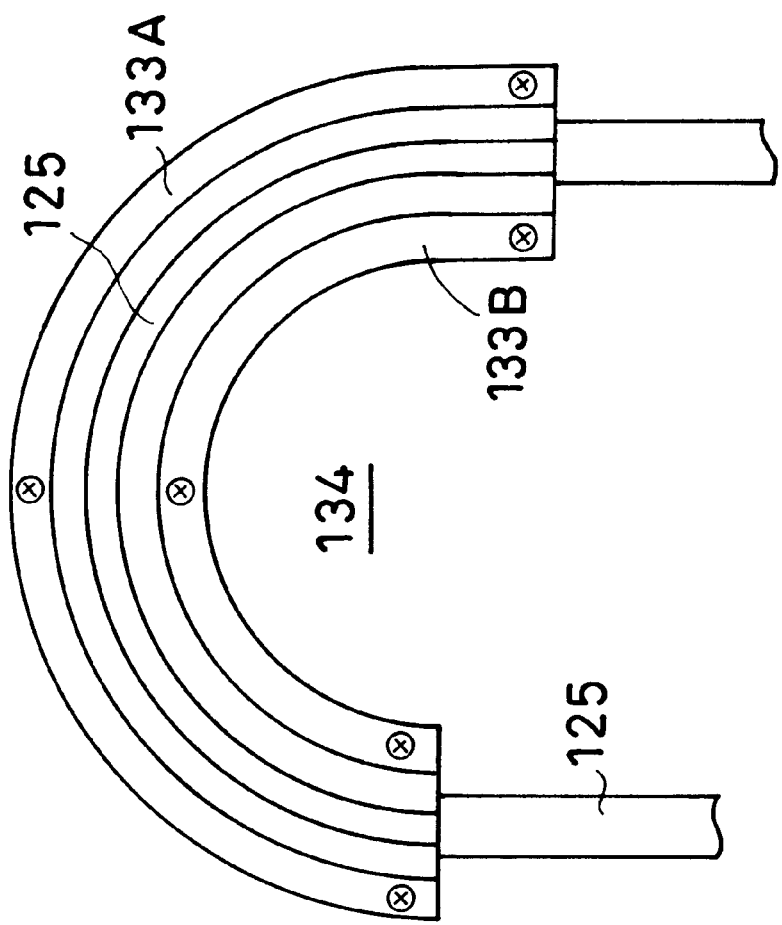
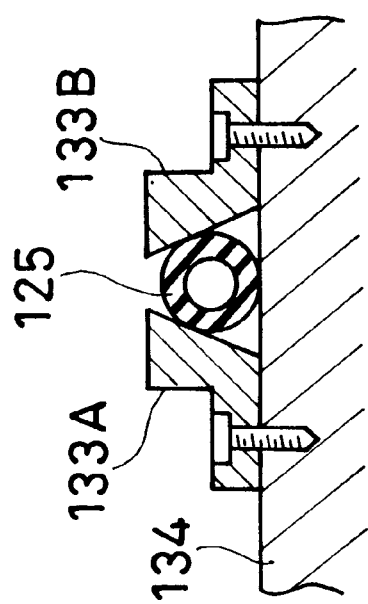

ENDOSCOPE FLUID CONTROLLER

BACKGROUND OF THE INVENTION

This application claims the priority of Japanese Patent Applications No. 9-308035 filed on Oct. 22, 1997 and No. 9-311478 filed on Oct. 27, 1997 and No. 9-352264 filed on Dec. 5, 1997, and No. 9-364459 filed on Dec. 18, 1997 which are incorporated herein by reference.

1. Field of the Invention

The present invention relates to an endoscope fluid controller and, more particularly, to the configuration of open/close control and flow rate control of air in an air feed duct, water in a water feed duct, suction of a suction duct, and the like, which ducts are disposed in an endoscope.

2. Description of the Prior Art

FIG. 16 shows a conventional configuration of ducts in an endoscope and an electromagnetic valve unit. Referring to FIG. 16, in an endoscope 1, a water feed duct 2A, an air feed duct 3A, and suction duct (also used for a treatment tool insertion channel) 4A are disposed from a distal end section 1A to an operation section 1B. The suction duct 4A is also connected to a forceps port 5 disposed in the operation section 1B. As shown in the figure, the operation section 1B is provided with an air feed/water feed (A/W) switch 6, which is a two-stage switch, a suction (SUC) switch 7, and a photographing button 8. The control signals of the switches 6 and 7 are supplied to an electromagnetic valve unit 10 via a signal line (not shown). Also, to connect the electromagnetic valve unit 10 to the operation section 1B, a water feed duct 2B, an air feed duct 3B, and a suction duct 4B are provided in a cable.

The electromagnetic valve unit 10 is provided with five electromagnetic valves Va, Vb, Vc, Vd and Ve for opening/closing each duct, a pump 12, a control section 13, and a water feed tank 14. The water feed tank 14 is connected to the pump 12 via an air feed duct 3C, and also connected to the electromagnetic valve Va via a water feed duct 2C. Further, a suction duct 4C is connected with a suction tank 15 and a pump.

According to the aforementioned configuration, air is fed through the air feed duct 3 (A-C) by closing the electromagnetic valves Va and Vc and opening the valve Vb, and water is fed through the water feed duct 2 (A-C) by closing the electromagnetic valves Vb and Vc and opening the valve Va. The air and water are fed to an objective lens window and the like disposed in the distal end section 1A, by which the contamination etc. of the objective lens window can be removed. Also, suction is performed by closing the electromagnetic valve Ve and opening the valve Vd, by which the contents etc. in a body being observed are sucked and discharged through the suction duct 4 (A-C). An endoscope apparatus which carries out control of fluids by using the electromagnetic valves described above has been disclosed in Japanese Patent Application Laid-Open No. 1-297045, No. 1-310638, etc. Conventionally, there also exists an endoscope which is provided with a mechanical valve in each switch section without the use of the electromagnetic valve unit.

BRIEF SUMMARY OF THE INVENTION

However, for the aforementioned control of fluids in the endoscope ducts, only the control of whether air feed, water feed, or suction is executed or not is carried out, and variable control of air feed amount, water feed amount, and suction amount cannot be carried out in the prior art. For the air feed and water feed to the objective lens window, if the amount can be controlled variably, the contamination can be removed efficiently while considering the effect on the body being observed. In sucking the contents, if the amount can be controlled variably, the contents can be discharged in accordance with the situation. Thereupon, an endoscope which is easy to use can be obtained.

The present invention has been made to solve the above problem, and accordingly a first object of the present invention is to provide an endoscope fluid controller in which the flow rate of fluid in a duct can be controlled variably and an endoscope which is easy to use can be obtained.

Also, in the duct control using an electrical switch as described above, no means is provided to confirm the operated state or the operation state. In particular, when an electromagnetic valve is used, it cannot be said that a sure and smooth operation is secured sufficiently. Specifically, when a mechanical valve is disposed in the endoscope operation section as a valve control member, the operating body itself opens and closes the duct directly. Therefore, whether or not the air feed, water feed, etc. are performed actually can be judged to some degree from the sound, vibration, or the like transmitted from the endoscope itself via the finger etc. of the operator.

However, when an electrical control switch and electromagnetic valve are used, the flow state of fluid is not transmitted via the finger or the like, so that in some cases, the operation state cannot be confirmed surely and smoothly.

Also, in the treatment, operation, etc. using an endoscope, assistants and attendants are present in addition to the operator. If the assistant or other person can grasp the control state of the duct, the treatment and operation can be performed more smoothly.

A second object of the present invention is to provide an endoscope fluid controller in which the operator, assistant, or other person can easily confirm the control state of duct in clinical medicine, and the duct can be operated surely and smoothly.

Also, as the aforementioned electromagnetic valves Va to Ve, for example, pinch valves of a type such that a soft duct is collapsed by a pressing portion can be used. According to this pinch valve, the opening/closing portion is not clogged with contamination etc., and a cleaning brush can be passed through the valve portion, so that the cleaning in the ducts 2, 3 and 4 can be performed easily.

However, in the opening/closing of pinch valve in the suction duct 4, if the suction pressure is high, the soft duct is deformed so as to be collapsed, with the result that suction cannot be performed, or the suction amount is reduced. That is to say, at the time of suction start, the suction pressure in the duct increases, and if the sucked objects include a highly viscous substances, a suction force changes during suction, so that the soft duct itself is deformed by a negative pressure given momentarily to the interior of the soft duct. In particular, at the bent portion of the suction soft duct, deformation is easily produced because the duct has been distorted by the bending. Such collapse and deformation are easily produced by the deterioration of soft duct, too.

Such a problem of collapse and deformation of suction soft duct can be solved to some degree by hardening the soft duct itself. In this case, however, a good closed state cannot be secured by collapsing the duct with the pinch valve.

A third object of the present invention is to provide an endoscope fluid controller in which the collapse and deformation of suction soft duct etc. is prevented, and a sufficient suction amount can be secured.

Further, for example, in a laparoscope, which is one type of endoscope, various treatments and operations using an electrical surgical knife are sometimes performed while looking at the picture of the interior of body being observed, which is caught by an endoscope in a state in which the endoscope inserted in the body cavity is held by a holding device. At this time, it is sometimes more convenient that the assistant other than the operator (endoscope operator) controls the fluid in the ducts 2, 3 and 4.

However, the air feed/water feed (A/W) switch 6 and the suction (SUC) switch 7 for this operation control are disposed in the endoscope operation section, so that it is difficult for the assistant to operate the switches. There arise disadvantages that the assistant interferes with the operator and that misalignment of the insertion position of the endoscope occurs.

Also, the ducts of the endoscope are cleaned after its use. If the control switches for controlling the ducts are disposed at a position distant from the endoscope, the cleaning work can be performed easily.

A fourth object of the present invention is to provide an endoscope fluid controller in which when an endoscope is used as a laparoscope or the like, or when the duct is cleaned, the operation for the duct control can be performed from a distant position, and the degree of freedom of duct control operation is high.

SUMMARY OF THE INVENTION

To achieve the above first object, the present invention provides an endoscope fluid controller comprising: a soft duct disposed as part of a fluid duct in an endoscope; a regulating (shut-off) valve of a collapse type for changing the collapsing amount of the soft duct; and control means for variably controlling the flow rate in the duct by performing the control of the regulating valve. A plurality of collapse type regulating valves are disposed in series for one duct, and the flow rate in the duct can be variably controlled by selectively opening/closing the plurality of regulating valves.

According to this configuration, a plurality of regulating valves are installed for one soft duct constituting the air feed duct, water feed duct, suction duct, or the like. As this regulating valve, a pinch valve or the like is used, and the pinch valve is set so that the pushing amount of a pressing portion on the soft duct disposed in the pinch valve is different. Therefore, depending on what valve of the plurality of regulating valves is operated, the collapsing amount of soft duct changes. As a result, the flow rate is changed.

A regulating valve capable of changing the collapsing amount of soft duct arbitrarily is provided as the collapse type regulating valve, and the flow rate in the duct can be variably controlled by the control of collapsing amount of the regulating valve. According to this configuration, the flow rate in the duct can be variably controlled by one regulating valve.

When the suction amount is controlled, the. regulating valve may be disposed in the suction duct itself, but can be disposed on the atmosphere open duct side to change the flow rate similarly. In this case, inversely to the case where the regulating valve is disposed in the suction duct, the larger the collapsing amount is, the higher the suction flow rate is.

To achieve the above second object, the present invention provides an endoscope fluid controller comprising: a duct control unit having an electromagnetic valve; control means for opening/closing various ducts disposed in an endoscope by using the electromagnetic valve; and a display section or a sound generating section which indicates the operation state of each of the various ducts.

According to this configuration, lamps etc. indicating the operation state of air feed, water feed, and suction are disposed, for example, on the control panel of an electromagnetic valve unit as the duct control unit, and each operation state is indicated by the lamps. The operation state can also be told by using a buzzer etc. As a display section indicating the operation state of each of various ducts, a monitor for showing a picture of the interior of body being observed can be used. Also, the display section can simultaneously indicate the flow rate of each of the various ducts together with the operation state of duct.

To achieve the above third object, the present invention is characterized in that a duct deformation preventive member for preventing the deformation of duct shape is disposed at a portion of the soft duct other than the portion of the regulating valve. Preferably, a hard covering member for preventing the duct deformation, having an inside diameter slightly larger than the outside diameter of the soft duct, is disposed around the soft duct as the duct deformation preventive member. Also, an adhesion spring can be disposed as a covering member for preventing the duct deformation.

According to this configuration, a tubular covering member consisting of an adhesive spring, hard pipe, or the like, having an inside diameter approximately equal to the outside diameter of the soft duct, is disposed around the soft duct, by which the collapsing deformation of the soft duct can be prevented. Also, as the duct deformation preventive member, a member other than the tubular one, for example, a guide member etc. having a groove whose cross-sectional shape is trapezoidal, triangular, square, etc. can be used.

To achieve the above fourth object, the present invention provides an endoscope fluid controller comprising: a first control switch disposed in an endoscope operation section; control means for controlling the fluid in various ducts disposed in an endoscope based on the operation of the first control switch; and a second control switch for controlling a fluid by using the control means, which is disposed on the control equipment side to which the endoscope is connected separately from the first control switch. In this case, a permission switch for making the operation of the second control switch effective is preferably disposed on the endoscope side.

BRIEF DESCRIPTION OF THE DRAWINGS

FIG. 10 is a view showing the whole configuration of an endoscope apparatus of the fourth embodiment;

FIGS. 14(A) and 14(B) are views showing a duct deformation preventive member in accordance with a sixth embodiment;

DETAILED DESCRIPTION OF THE PREFERRED EMBODIMENTS

First Embodiment

Figure 1:
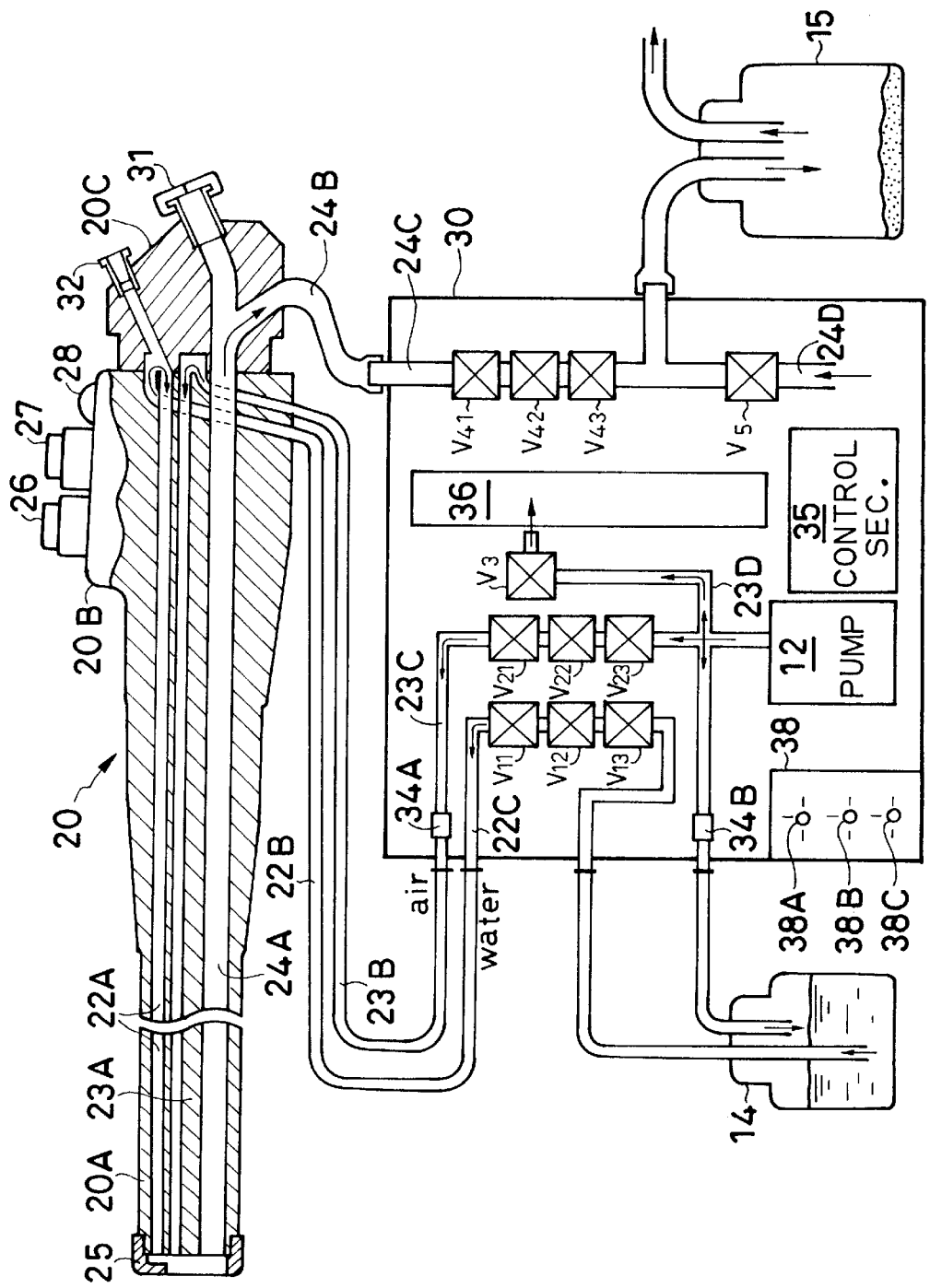
FIG. 1 is a schematic view showing a configuration of an endoscope to which an endoscope fluid controller in accordance with a first embodiment of the present invention is applied.
Figure 2:
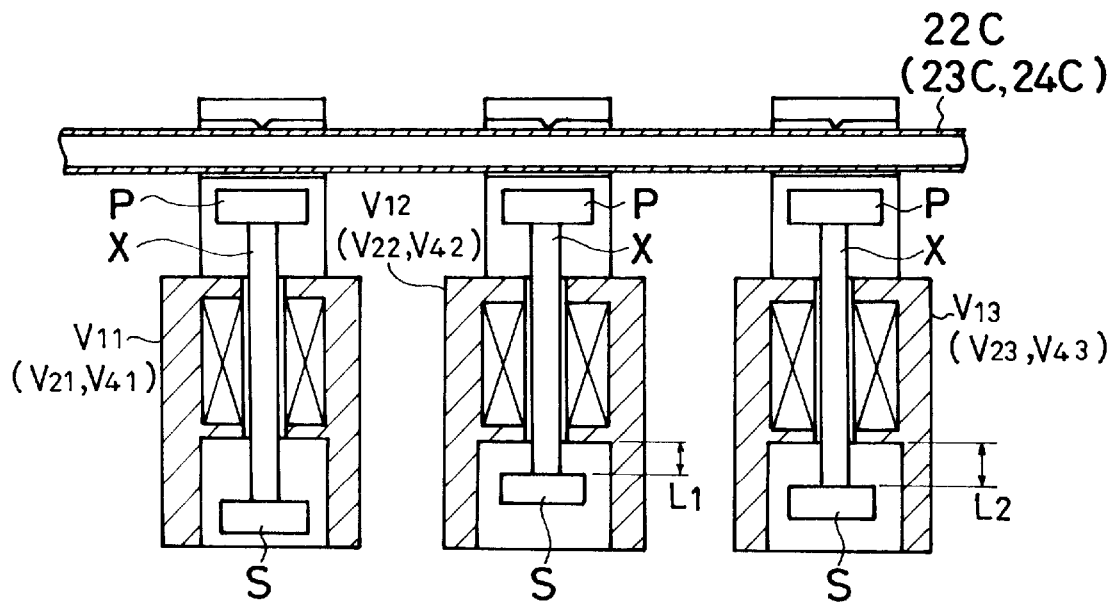
FIG. 2 is a view showing a configuration of a set of pinch valves for each duct shown in FIG. 1.

FIGS. 1 and 2 show a configuration of an endoscope fluid controller in accordance with a first embodiment. Referring to FIG. 1, in an endoscope (electronic endoscope) 20, a water feed duct 22A, an air feed duct 23A, and a suction duct 24A are disposed from a distal end section 20A to an operation section 20B. At the tip end of the endoscope distal end section 20A, a cap 25 is removable attached, and the cap 25 is provided with a nozzle or the like for feeding air and water to an observation window (a lens window of objective optical system).

As shown in the figure, the operation section 20B is provided with an air feed/water feed switch 26, which is a two-stage switch, a suction switch 27, and a photographing button 28. The control signals of the switches 26 and 27 are supplied to an electromagnetic valve unit 30. Also, to connect the electromagnetic valve unit 30 to the operation section 20B, a water feed duct 22B and an air feed duct 23B are provided in a cable.

A duct unit 20C is provided on the rear side of the operation section 20B. By a folding portion formed when the duct unit 20C is connected, the water feed ducts 22A and 22B are connected to each other, and the air feed ducts 23A and 23B are connected to each other. The duct unit 20C is fitted with a suction duct 24B extending to the electromagnetic valve unit 30, and the suction duct 24B is provided with a forceps port 31 separating from a halfway position. A member 32 shown in the figure, which is connected to the water feed duct 22A, is a lens surface flushing port for feeding air and water by mounting a syringe or the like when the degree of contamination on the lens of the observation window is high.

The electromagnetic valve unit 30 is provided with a pump 12, a control section 35, and a power source 36, and connected with a water feed tank 14 and a suction tank 15. In order to carry out the flow rate control of the ducts 22, 23, and 24, three pinch valves (electromagnetic valves) V11, V12 and V13 are disposed in series at a soft duct portion of the water feed duct 22C, similar pinch valves V21, V22 and V23 are disposed in series at a soft duct portion of the air feed duct 23C, and similar pinch valves V41, V42 and V43 are disposed in series at a soft duct portion of the suction duct 24C. Like the conventional electromagnetic valve unit, an electromagnetic valve V3 is attached to an atmosphere open duct 23D for feeding air and water, and an electromagnetic valve V5 is attached to an atmosphere open duct 24D for suction.

FIG. 2 shows a configuration (opening operation time) of the aforesaid three pinch valves V11 to V13. The pinch valve V has a pressing portion P disposed at the tip end of a shaft X and a stopper S at the rear end. These elements are moved longitudinally by an electromagnetic force so that the water feed duct (soft duct) 22C is collapsed. The stopper S of the left-side valve V11 is disposed at a position such that the pressing portion P completely collapses the soft duct 22C to close the duct at the time of closing operation. The stopper S of the center valve V12 is disposed at a position of a length L1 from the abutting face of the body side at the time of closing operation. The stopper S of the right-side valve V13 is disposed at a position of a length L2 (L2>L1) from the abutting face at the time of closing operation.

Figure 3:
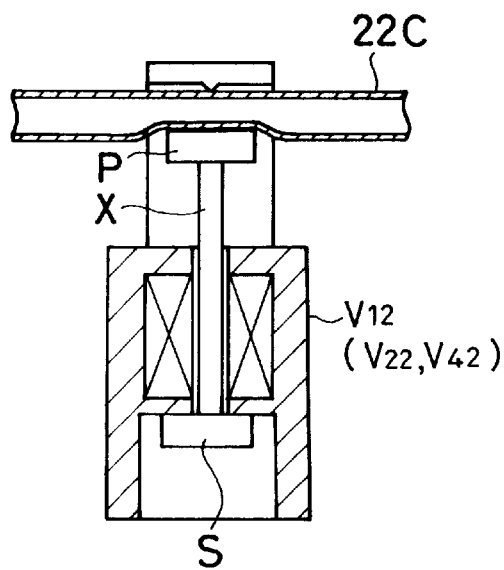
FIG. 3 is a view showing an operation state of the pinch valve shown in FIG. 2.

FIG. 3 shows a state of the pinch valve V12 at the time of closing operation. As shown in the figure, when the valve V12 is operated, the pressing portion P is stopped halfway by the stopper S without completely collapsing the soft duct (22C). Therefore, the water flow rate in the water feed duct 22C is made lower than that at the full open time because the duct is collapsed halfway. Also, for the right-side pinch valve V13, the water flow rate is further decreased because the soft duct is collapsed heavier than the case of the valve V12. It is to be noted that the pinch valve V11 sets the full open maximum flow rate at the time of opening operation.

On the other hand, the pinch valves V21, V22, V23, V41, V42 and V43 disposed in the air feed duct 23C and the suction duct 24C operate in the same way. In this example, for example, "high" (full open), "medium", and "low" flow rates can be set. When the flow of the duct 22, 23 or 24 is to be stopped, it is necessary only that the pinch valve V11, V21 or V41 is closed. Also, the number of the arranged pinch valves V is arbitrary; the larger the number is, the more finely the flow rate can be controlled.

Further in FIG. 1, a flow rate control switch section 38 is provided on the control panel of the electromagnetic valve unit 30. By operating a water amount switch 38A, an air amount switch 38B, and a suction amount switch 38C in the flow rate control switch section 38, the flow rate of the ducts can be controlled stepwise.

The first embodiment is configured as described above. When the air feed/water feed switch 26 is not operated, the pinch valves V11 and V21 are closed, and the electromagnetic valve V3 is open, so that the air sent from the pump 12 is discharged to the atmosphere through the atmosphere open duct 23D. When the water feed operation (for example, first-stage pressing) is performed by using the air feed/water feed switch 26, the opening/closing control of the pinch valves V11, V12 and V13 is carried out so that a flow rate set by the water amount switch 38A is obtained. Specifically, when "high" flow rate is set, the valve V11 is opened (V12 and V13 are also opened). When "medium" flow rate is set, only the valve V12 is closed (V11 and V13 are open). When "low" flow rate is set, only the valve V13 is closed (V11 and V12 are open). Thus, water is fed with the selected flow rate.

Also, when the air feed operation (for example, second-stage pressing) is performed by using the air feed/water feed switch 26, or when the suction operation is performed by using the suction switch 27, the opening/closing control of the pinch valves V21, V22, V23, V41, V42 and V43 is performed in the same way as described above, so that air feed and suction can be executed with the three-stage flow rate.

Figure 4:
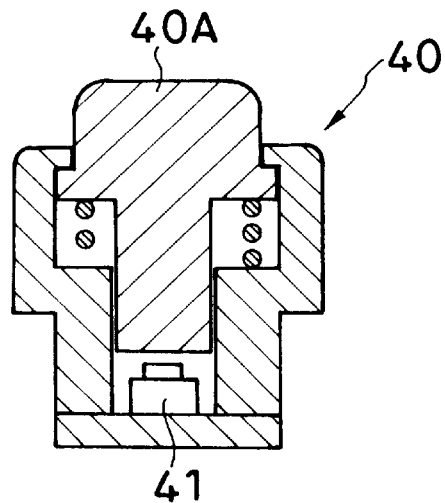
FIG. 4 is a sectional view showing a configuration of a control switch, which is disposed in an endoscope operation section, for carrying out flow rate control.

FIG. 4 shows a configuration of a control switch for flow rate control, which is disposed in the endoscope operation section 20B. Although the switch 38 for flow rate control of air feed, water feed, and suction is provided in the electromagnetic valve unit 30 in the above embodiment, this flow rate control can be performed by disposing the control switch 40 shown in FIG. 4 in the endoscope operation section 20B as the air feed switch, water feed switch, and suction switch.

Specifically, as shown in FIG. 4, the control switch 40 is configured so that a pressure sensitive sensor 41 is pushed by a vertically moving operating body (push button) 40A. As the pressure sensitive sensor 41, a pressure sensitive diode, pressure sensitive transistor, piezo-type micromachine silicon device, and the like can be used. According to this control switch, the pressing force of the operating body 40A is detected stepwise. If the opening and closing of the pinch valves V11, V12, V13, V21, V22, V23, V41, V42 and V43 are controlled according to this stepwise operation pressure, the flow rate can be controlled variably in a stepwise manner. Also, this control switch 40 may detect the operation stroke amount stepwise, not detecting the pressure. In this case, the flow rate can be controlled by the stepwise stroke amount.

Figures 5A, 5B:
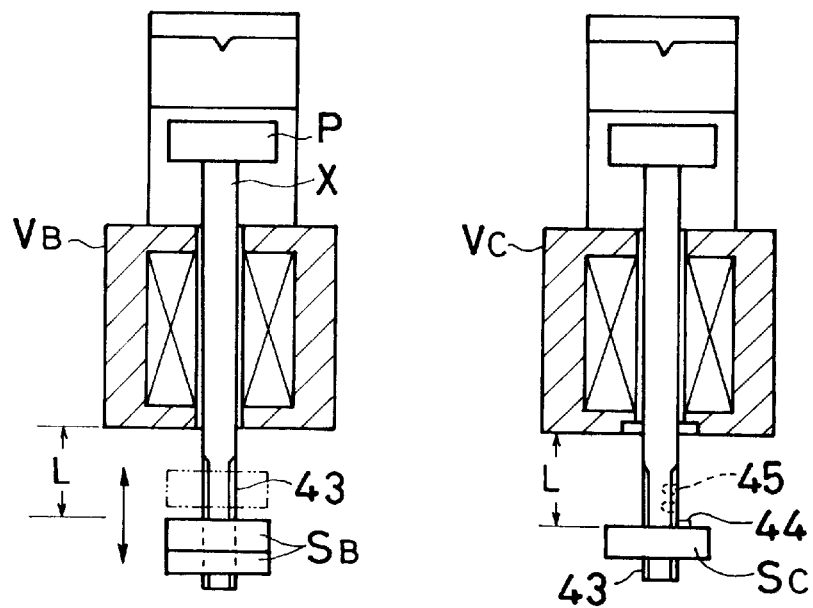
FIGS. 5(A) and 5(B) are views showing other configurations of pinch valves of the embodiment.

FIG. 5 shows other example of configurations in which the collapsing amount of the aforementioned plurality of pinch valves V is variable. For a pinch valve VB shown in FIG. 5(A), an external thread portion 43 is formed on the rear end side of a shaft X. A stopper SB consisting of double nuts is attached to the external thread portion 43. For a pinch valve VC shown in FIG. 5(B), a pin 44 is put into a pinhole 45 to perform the positioning of a stopper SC. By this configuration, the length L from the stopper SB, SC to the abutting face can be changed to a predetermined value easily.

Second Embodiment

Figure 6:
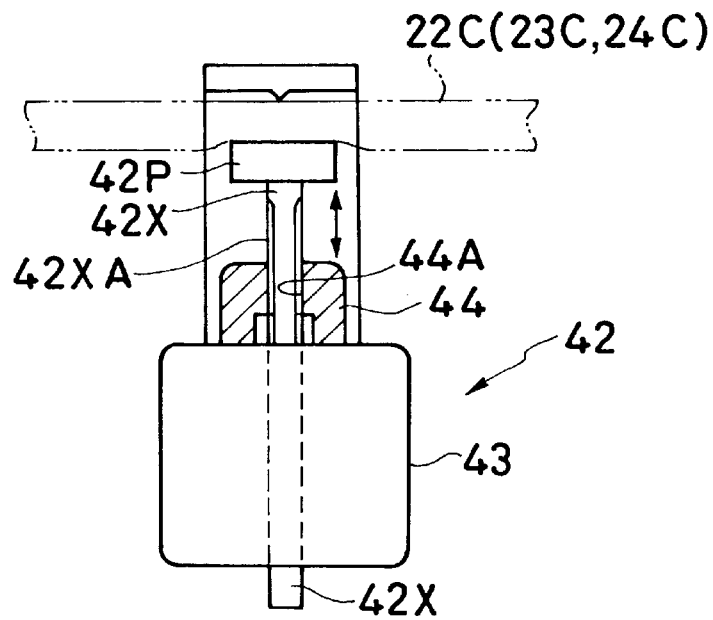
FIG. 6 is a view showing a configuration of a regulating valve in accordance with a second embodiment.

FIG. 6 shows a configuration of a second embodiment in which the collapsing amount is changed arbitrarily by one regulating valve. A regulating valve 42 shown in the figure uses a stepping motor. A shaft 42X connected to a pressing portion 42P is disposed as a rotating shaft of a stepping motor portion 43, and is formed with an external thread portion 42XA on the tip end side thereof. On the front side of the stepping motor portion 43, a bearing portion 44 formed with an internal thread portion 44A is provided.

According to this regulating valve 42, the pressing portion 42P is moved longitudinally by an amount corresponding to the number of revolutions of the shaft 42X by the stepping motor portion 43, so that the projection amount of the pressing portion 42P can be controlled variably by the control of the number of revolutions. Therefore, in the second embodiment, the collapsing amount of the water feed soft duct 22C (air feed soft duct 23C, suction soft duct 24C) is changed by one regulating valve 42, by which the flow rate can be controlled.

To variably change the collapsing amount arbitrarily, various configurations other than this valve can be applied. For example, in the regulating valve shown in FIGS. 2 and 3, the configuration may be such that a plurality of locking members consisting of, for example, a pin-shaped member are provided in the vertical direction of the outside wall of the stopper S, and these locking members are selectively protruded to the center side by an electrical means (for example, electromagnetic solenoid) so that the stopper S can be locked at different positions in the moving direction of the shaft X.

Third Embodiment

Figure 7:
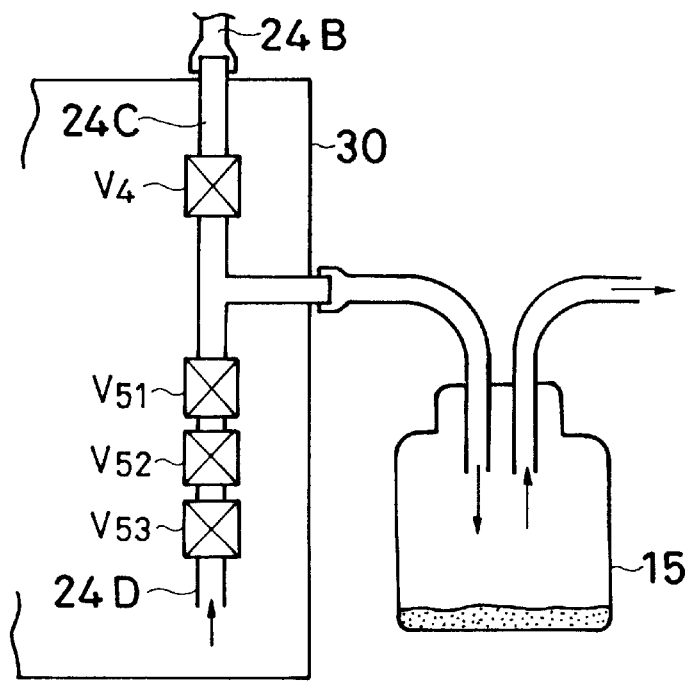
FIG. 7 is a view showing a configuration of flow rate control of a suction duct in an endoscope apparatus of a third embodiment.

FIG. 7 shows a configuration of a third embodiment in which the flow rates of the suction duct 24 is controlled. In this third embodiment, as shown in the figure, the suction duct 24C is provided with an electromagnetic valve V4 which is the same as that of the conventional apparatus, and the atmosphere open duct 24D is provided with pinch valves V51, V52 and V53 with a different collapsing amount. These valves V51, V52 and V53 can be configured in the same way as the valves V11, V12 and V13 shown in FIG. 2.

According to the third embodiment, by opening any of the pinch valves V51, V52 and V53 while the electromagnetic valve V4 is open, four-stage control of the flow rate can be carried out. Specifically, the flow rate increases in the order of the time when the valve V51 (V11) is opened, the time when the valve V52 (V12) is opened, the time when the valve V53 (V13) is opened, and the time when the valve V51 (V11) is closed. Therefore, in the case of the flow rate control of the suction duct 24, the configuration in which the valves V are disposed on the side of the atmosphere open duct 24D has an advantage that the number of controls of the flow rate increases by one, as compared with the first embodiment. It is to be noted that the regulating valve in the second embodiment may be used.

As described above, by controlling the regulating valve of a type such that the soft duct is collapsed, the flow rate of the fluid in various ducts can be controlled variably. As a result, in the case of the air feed/water feed operation, the contamination can be removed efficiently while considering the effect on the body being observed. In the case of sucking operation, the contents can be discharged in accordance with the situation. Thereupon, an endoscope, which is easy to use, can be obtained.

Fourth Embodiment

Figure 8:
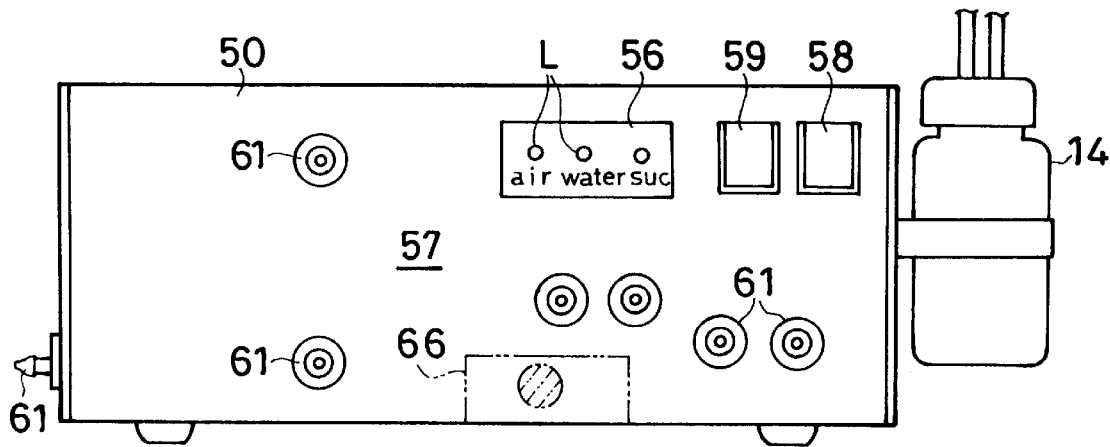
FIG. 8 is a view showing a configuration of an electromagnetic valve unit (duct control unit) in an endoscope apparatus in accordance with a fourth embodiment.
Figure 16:
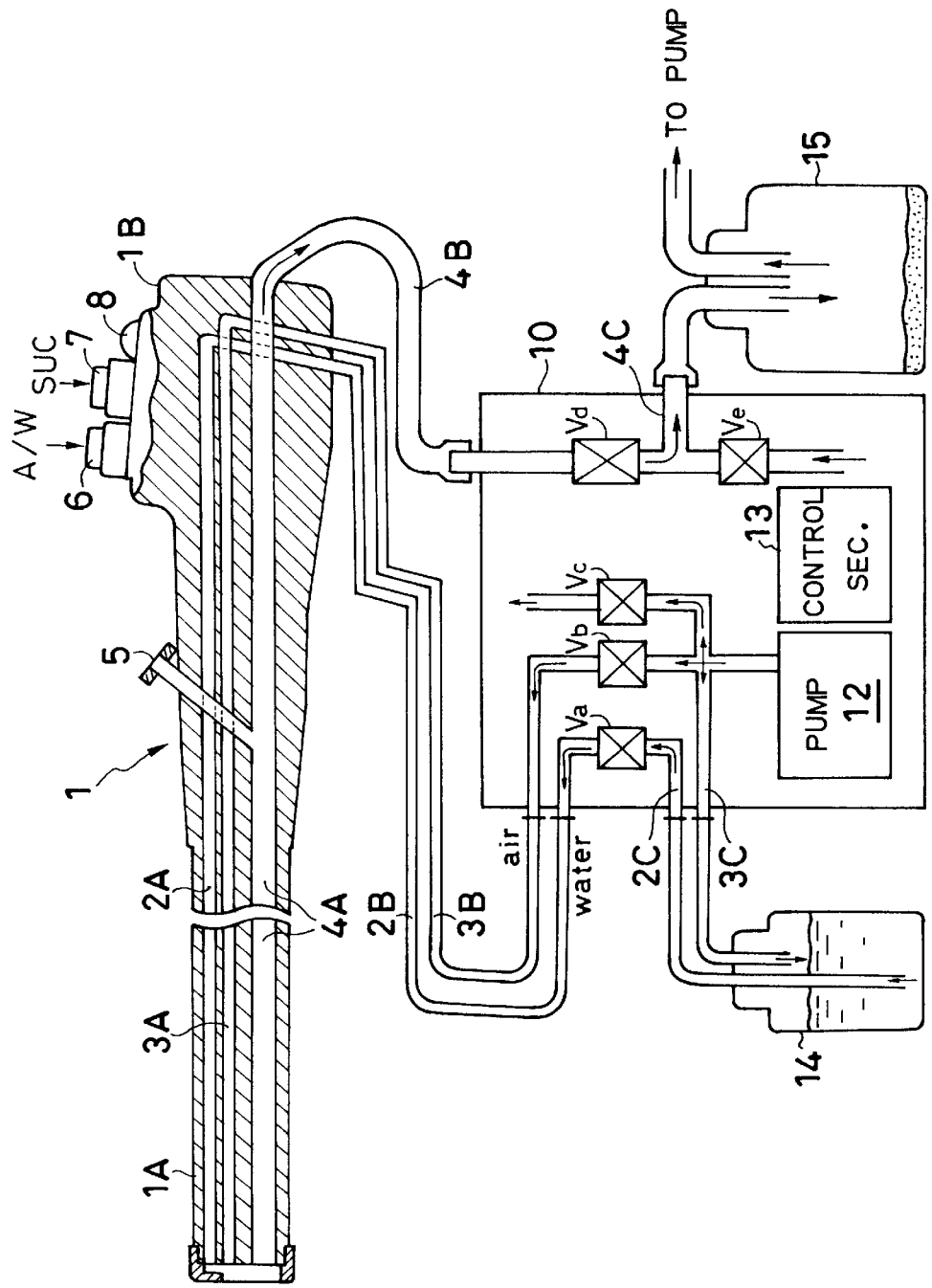
FIG. 16 is a view showing a configuration of a conventional endoscope fluid controller.

FIG. 8 shows a configuration of an electromagnetic valve unit in accordance with a fourth embodiment, FIG. 9 shows a configuration of a duct operation display section on a control panel, and FIG. 10 shows a whole configuration of an endoscope apparatus of this embodiment. In FIG. 10, the configuration of an electronic endoscope 1 and the configurations of ducts 2, 3 and 4 are the same as those in FIG. 16.

An electromagnetic valve unit 50 of this embodiment is provided with, for example, five electromagnetic valves (pinch valves and diaphragm valves) V1, V2, V3, V4 and V5 for opening/closing each duct, a pump 12, a control section 55, and so on. A suction duct 4C is connected with a suction tank 15 and a pump. Therefore, by closing the electromagnetic valves V1 and V3 and opening the valve V2, air is fed through an air feed duct 3, and by closing the electromagnetic valves V2 and V3 and opening the valve V1, water is fed through a water feed duct 2. Also, by closing the electromagnetic valve V5 and opening the valve V4, suction is performed.

The control section 55 receives an on/off signal from an air feed/water feed switch 6 and a suction switch 7 to perform opening/closing operation of the electromagnetic valves V1 to V5, and also carries out control for displaying the operation state. A display section 56, which is connected to the control section 55 and has lamps, is disposed on the control panel of the electromagnetic valve unit 50.

FIG. 8 is a view showing the control panel 57 side of the electromagnetic valve unit 50. On this control panel 57, a power switch 58 and a pump switch 59 are arranged, and the display section 56 is provided. At a predetermined position of an outside wall of the electromagnetic valve unit 50, a plurality of connectors 61 f or connection to various ducts are arranged.

Figure 9A:
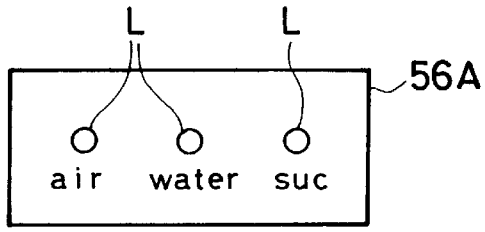
FIGS. 9(A), 9(B) and 9(C) are views showing examples of duct operation display sections on a control panel of an electromagnetic valve unit of the fourth embodiment.
Figure 9B:
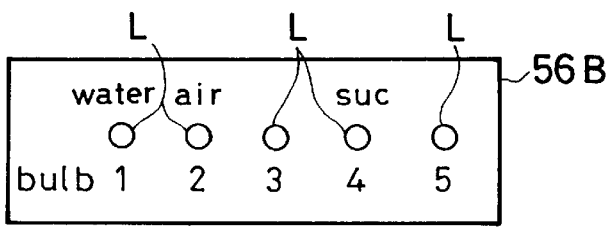
Figure 9C:
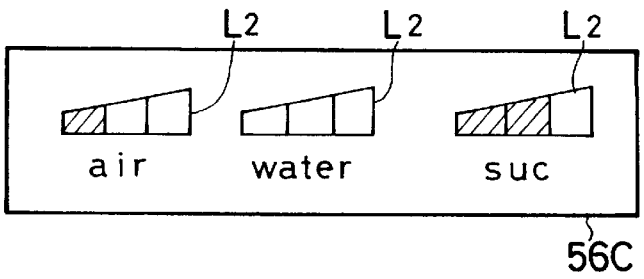

FIGS. 9(A), 9(B) and 9(C) show typical configurations of the display section 56. In FIG. 9(A), three lamps (for example, LEDs) L indicating air (airfeed), water (water feed), and suc (suction) are provided. At the time of operation, the corresponding lamp L can be turned on. In FIG. 9.(B), lamps L indicating the number 1 to 5 (corresponding to V1 to V5) of bulb (electromagnetic valve) are provided, and indications of the aforesaid air, water and suc are also provided for the lamps L. In this case, the opened valve is indicated by the lighting of the lamp.

In FIG. 9(C), the f low rate is indicated at the same time. As shown in the figure, an indicator (LED etc.) group L2 provided with three divided regions showing the high/low level is provided. In this case, the flow rate of three stages of high, medium, and low of the operating air (air feed), water (water feed), and suc (suction) is indicated by the lighting of lamp.

In this embodiment, in addition to the display section 56 provided in the electromagnetic valve unit 50 as described above, a monitor provides the same display. Specifically, as shown in FIG. 10, the control section 55 in the electromagnetic valve unit 50 supplies information signals regarding the operation state of ducts to an image processing processor 63 disposed in an external processor unit or the like. This image processing processor 63 image-processes the video signals obtained by a CCD at the distal end section of the endoscope, and also performs processing for putting a mask, for example, at the outer periphery. At the same time, a display section showing the operation state of the ducts 2, 3 and 4 is displayed in the mask portion.

Figure 11:
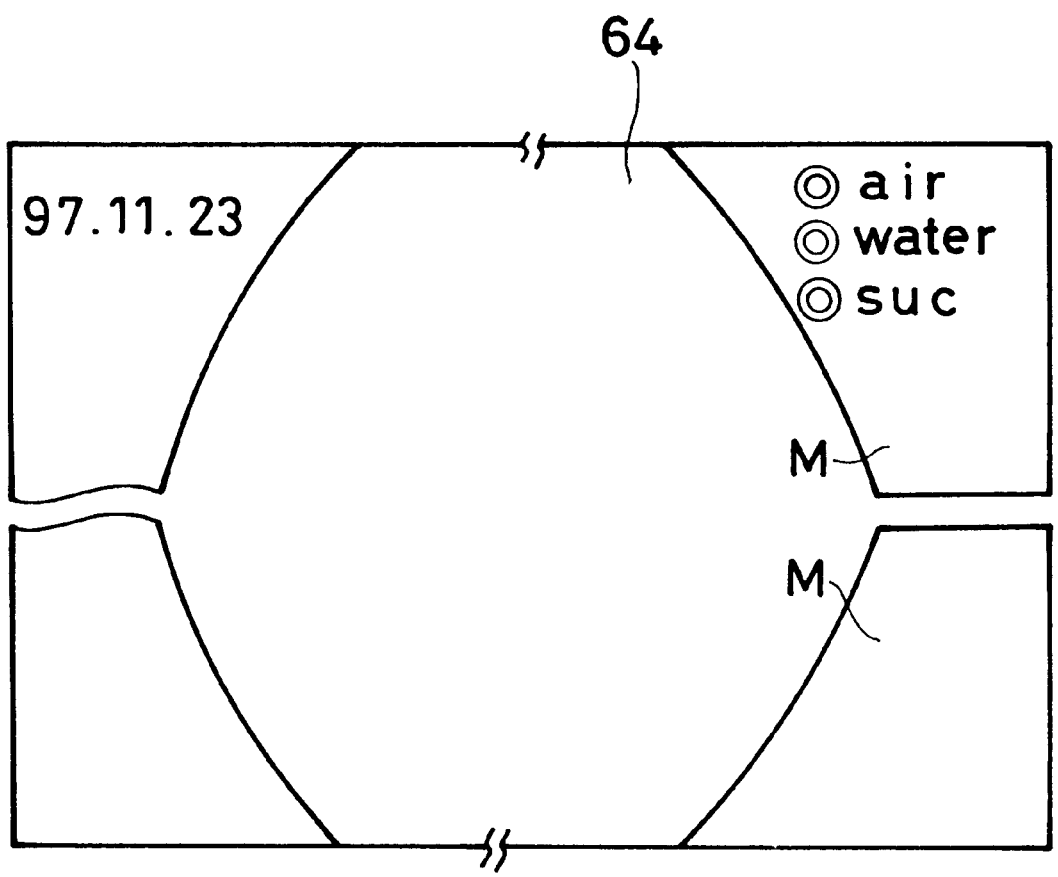
FIG. 11 is an explanatory view showing a duct operation display section of a monitor shown in FIG. 10.

FIG. 11 shows a screen of the monitor 64. As shown in the figure, characters of air, water, and suc and lamp portions of small circles are indicated in the mask portion M at the upper right of the screen. Therefore, by turning on any of the lamp portions, the operation state is displayed. As this image display, various displays can be applied. For example, the lamp portions are not provided, and only the characters may be lighted. Also, when the flow rate is displayed, the level display, which is the same as that shown in FIG. 9(C), can be provided.

This embodiment is configured as described above. In FIG. 10, when, for example, a first stage of the air feed/water feed switch 6 is pressed, the electromagnetic valve V1 is opened and the electromagnetic valves V2 and V3 are closed by the control section 55, by which water is fed. At the same time, the control section 55 supplies a lighting control signal to the display section 56, so that as shown in FIG. 9(A), the lamp L of "water" in the display section 56 is turned on. Also, when a second stage of the air feed/water feed switch 6 is pressed, the electromagnetic valve V2 is opened and the electromagnetic valves V1 and V3 are closed, by which air is fed, and the lamp L of "air" in the display section 56 is turned on.

Further, when the suction switch 7 is pressed, the electromagnetic valve V5 is closed, and the electromagnetic valve V4 is opened, by which suction is performed through the suction duct 4 (A-C), and the lamp L of "suc" is turned on. In this embodiment, a duct operation information signal is supplied from the control section 55 to the image processing processor 63. This processor 63 performs display on the monitor 64 according to the operation state, and as shown in FIG. 11, the corresponding small circle lamp portion of the operation character is turned on. Thus, the operator or the assistant can easily confirm the operation state of duct by looking at both of the display section 56 on the control panel of the electromagnetic valve unit 50 and the screen of the monitor 64, so that he/she can perform the operation of duct surely and smoothly.

Also , in the example of FIG. 9(B), the operation state of air feed, water feed, and suction together with the number of the electromagnetic valve V can be confirmed. In this duct control, the flow rate can be changed. In this case, as shown in FIG. 9(C), the operation state of air feed, water feed, etc. to gether with the magnitude of flow rate can be confirmed. In FIG. 10, in the standby state, the electromagnetic valve V3 is opened, so that air is discharged through the atmosphere open duct 3D. Also, the electromagnetic valve V5 is opened, so that air is sucked through the atmosphere open duct 4D.

Although the operation state is displayed by the display section 56 such as lamps L in this embodiment, the operation state may be noticed by a sound generating section such as a buzzer. Specifically, as shown in FIGS. 8 and 10, a buzzer-generating portion 66 is provided so as to receive a control signal from the control section 55. This buzzer-generating portion 66 generates a sound by which, for example, air feed, water feed, and suction can be identified (by changing the number of times, period of time, tone quality, etc.). Alternatively, the buzzer-generating portion 66 is configured so as to generate the same sound and generates it only at the operation start time (or both of the start time and the finish time). Such buzzer generation can also tell the operation state of each duct.

Fifth Embodiment

Figure 12:
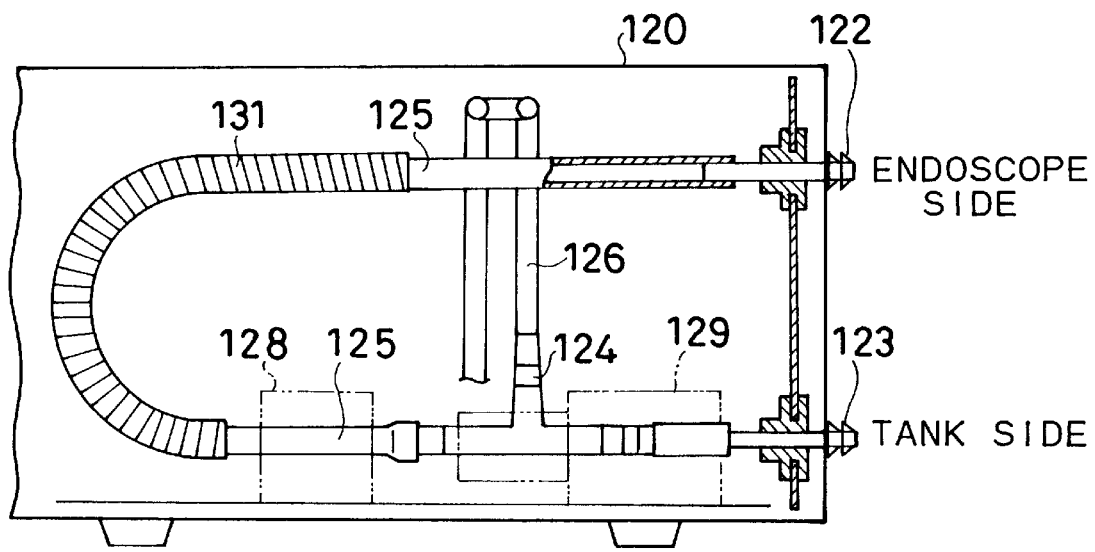
FIG. 12 is a side view showing a configuration in an electromagnetic valve unit in accordance with a fifth embodiment.
Figure 13:
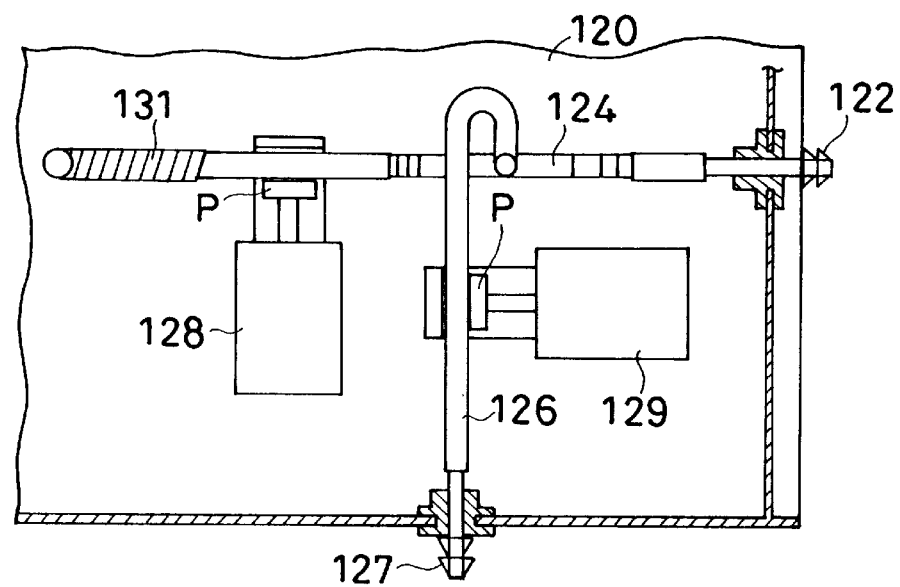
FIG. 13 is a top view of the apparatus shown in FIG. 12.

FIG. 12 is a side view of an electromagnetic valve unit in accordance with a fifth embodiment, and FIG. 13 is a top view of FIG. 12. This electromagnetic valve unit 120 is connected to the endoscope shown in FIGS. 1 and 10.

Referring to FIGS. 12 and 13, in the electromagnetic valve unit 120, a suction soft duct 125 consisting of a silicon resin tube or the like is attached via a branch duct 124 between a connection port 122 on the endoscope side and a connection port 123 on the tank side. Also, an atmosphere open duct 126 (similarly consisting of a silicon resin tube) branches from the branch duct 124, and the atmosphere open duct 126 extends to a discharge duct 127. A pinch valve 128 is disposed on the suction soft duct 125, and a pinch valve 129 is disposed on the atmosphere open duct 126. For the pinch valves 128 and 129, a pressing portion P is moved by an electromagnetic force to collapse the ducts 125 and 126, respectively, by which the duct is closed.

As shown in the figures, an adhesion spring 131, which is a covering member for preventing the deformation of duct, is provided at the outer periphery of the suction soft duct 125. This adhesion spring 131 is a spring wound in a coil form in an adhering manner, and its inside diameter is slightly larger than the outside diameter of the suction soft duct 125 (almost the same diameter). The adhesion spring 131 is disposed at the bent portion and straight port ion of the suction soft duct 125.

According to the adhesion spring 131, when the duct 125 is to be collapsed by a suddenly increasing suction pressure, the expansion of the duct wall to the outside is restricted, whereby the deformation of the duct shape (cross-sectional circular shape) of the suction soft duct 125 is prevented. In particular, at the bent portion as shown in FIG. 12, since distortion is produced on the suction soft duct 125, the duct shape is easily deformed by the suction pressure. Similarly, when the soft duct 125 has been deteriorated, the deformation occurs easily. In these cases, the adhesion spring 131 prevents the collapse and deformation satisfactorily. As a result, a phenomenon that the suction amount is reduced, or the suction itself becomes impossible can be eliminated.

Although an example in which the adhesion spring 131 is provided as a member for preventing the duct deformation has been explained in the above fifth embodiment, a plastic hard pipe or the like may be used in place of the adhesion spring 131.

Sixth Embodiment

FIGS. 14(A) and 14(B) show a sixth embodiment which is another example of a member for preventing the duct deformation. In this example, guide portions 133A and 133B are used, which are formed with a trapezoidal (or triangular) groove between them. As shown in the figures, a suction soft duct 125 is put on a support portion 134 so as to be in contact with the support portion 134, and the guide portions 133A and 133B are disposed so as to hold the soft duct 125 from both sides. Specifically, the respective guide portions 133A and 133B have a slant surface formed so as to spread on the bottom side, and the guide portions 133A and 133B are disposed so that the slant surface comes into contact with the soft duct 125 from both sides. The guide portions 133A and 133B are fixed to the support portion 134 with screws, adhesive, or the like.

In the sixth embodiment as well, the collapse of the soft duct 125 can be prevented. In this embodiment, since the guide portions 133A and 133B are separate members, the width of the inside groove formed by them can be adjusted, and the optimum positioning with respect to the soft duct 125 is secured, and also the guide portions 133A and 133B can accommodate the soft duct 125 with a different outside diameter. The guide portions 133A and 133B may be formed integrally, and the shape of the groove may be a square.

Seventh Embodiment

Figure 15:
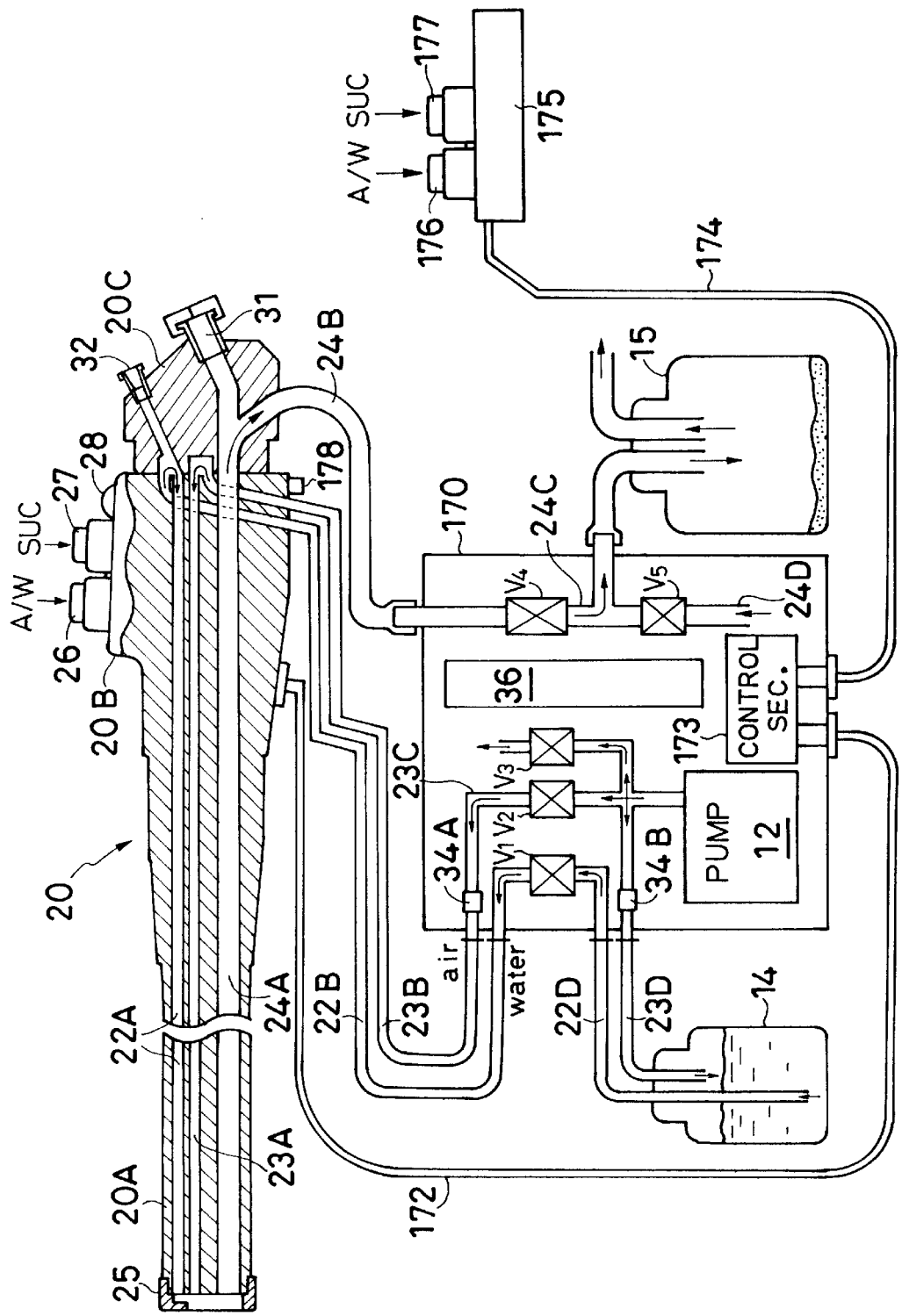
FIG. 15 is a view showing the whole configuration of an endoscope apparatus in accordance with a seventh embodiment.

FIG. 15 shows an endoscope fluid controller in accordance with a seventh embodiment. As shown in the figure, the main configuration of the ducts in an endoscope 20 and electromagnetic valve unit 170 is the same as that of the aforementioned embodiments. An operation section 20B is provided with an air feed/water feed (A/W) switch 26 and a suction (SUC) switch 27. The control signals of the switches 26 and 27 are supplied to an electromagnetic valve unit 170 via a signal line 172. In the electromagnetic valve unit 170, five electromagnetic valves V1 to V5 for opening/closing each duct and a control section 173 are provided.

An auxiliary operationelection 175 is connected to the electromagnetic valve unit 170 via a signal line 174. The auxiliary operation section 175 is provided with a second air feed/water feed switch (two-stage switch) 176 and a second suction switch 177, which have the same functions as those of the air feed/water feed switch 26 and the suction switch 27 on the endoscope operation section 20B. The control signals of the switches 176 and 177 are sent to a control section 173 via the signal line 174. A second photographing button may be provided in this auxiliary operation section 175.

Further, the endoscope operation section 20B is provided with a permission switch 178 for making the operation of the second air feed/water feed switch 176 and suction switch 177 effective. That is to say, in this embodiment, the second switches 176 and 177 are not always effective, but they are effective only when the operator turns on the permission switch 178, by which an unnecessary operation is avoided.

According to the above-described configuration, after the permission switch 178 on the endoscope operation section 20B side is turned on, when the air feed (first stage) operation is performed by using the second air feed/water feed switch 176 in the auxiliary operation section 175, the electromagnetic valves V1 and V3 are closed and the valve V2 is opened, by which air is fed through an air feed duct 23. Also, when the water feed (second stage) operation is performed by using the second air feed/water feed switch 176, the electromagnetic valves V2 and V3 are closed and the valve V1 is opened, by which water is fed through a water feed duct 22. The air feed/water feed is performed with respect to an objective lens window and the like disposed at a distal end section 20A, whereby the contamination etc. of the objective lens window can be removed. At the standby time, only the electromagnetic valve V3 is opened, by which air is discharged to the atmosphere.

On the other hand, when the second suction switch 177 in the auxiliary operation section 175 is operated, the electromagnetic valve V5 is closed and the valve V4 is opened, by which suction is performed through a suction duct 24. Thereby, the contents etc. in the body being observed are sucked through the suction duct 24, and recovered into a suction tank 15. At the time of standby of the suction switch 177, only the electromagnetic valve V5 is opened, by which the atmosphere is sucked.

When the permission switch 178 in the endoscope operation section 20B is turned off, operation is not performed even if the second air feed/water feed switch 176 and suction switch 177 are operated.

Thus, according to the seventh embodiment, the degree of freedom of operation of air feed, water feed, and suction is increased. In particular, when the endoscope is used as a laparoscope or the like, or when the duct is cleaned, the operation can be performed from a distant position, which provides greater ease of use.

Although the auxiliary operation section 175 is disposed via the signal line 174 in the above embodiment, the auxiliary operation section may be disposed directly on the control panel etc. of the electromagnetic valve unit 170. Also, the permission switch 178 may be disposed at other places in the electromagnetic valve unit 170 or the like. Also, as the control switches 176 and 177, the control switch 40 or 42 shown in FIG. 4 or 6 may be provided.

what is claimed is:

1. An endoscope fluid controller comprising:
   a soft duct disposed as part of a fluid duct in an endoscope;
   a regulating valve of a collapse type for changing the collapsing amount of the soft duct; and
   control means for variably controlling the flow rate in the duct by performing the control of the regulating valve, wherein a plurality of collapse type regulating valves are disposed in series for the duct, and the flow rate in the duct is variably controlled by selectively opening/closing the plurality of regulating valves.

2. An endoscope fluid controller according to claim 1, wherein, the regulating valve is disposed in an atmosphere open duct of a suction duct.

3. An endoscope fluid controller according to claim 1, wherein the soft duct is a suction soft duct; and a duct deformation preventive member for preventing the deformation of duct shape is disposed at a portion of the suction soft duct other than the portion of the regulating valve.

4. An endoscope fluid controller according to claim 1, wherein a regulating valve capable of changing the collapsing amount of soft duct arbitrarily is provided as the collapse type regulating valve, and the flow rate in the duct is variably controlled by the control of the collapsing amount of the regulating valve.

5. An endoscope fluid controller comprising:
   a soft duct disposed as part of a fluid duct in an endoscope;
   a regulating valve of a collapse type for changing the collapsing amount of the soft duct; and
   control means for variably controlling the flow rate in the duct by performing the control of the regulating valve, wherein a regulating valve capable of changing the collapsing amount of the soft duct arbitrarily is provided as the collapse type regulating valve, and the flow rate in the duct is variably controlled by the control of the collapsing amount of the regulating valve.

6. An endoscope fluid controller according to claim 5, wherein, the regulating valve is disposed in an atmosphere open duct of a suction duct.

7. An endoscope fluid controller according to claim 5, wherein the soft duct is a suction soft duct; and a duct deformation preventive member for preventing the deformation of duct shape is disposed at a portion of the suction soft duct other than the portion where the regulating valve is located.

8. An endoscope fluid controller comprising:
   a duct control unit having an electromagnetic valve;
   control means for opening/closing various ducts disposed in an endoscope by using the electromagnetic valve; and
   a display section or a sound generating section which indicates the operation state of each of the various ducts.

9. An endoscope fluid controller according to claim 8, wherein a monitor for showing a picture of the interior of body being observed is used as a display section indicating the operation state of each of the various ducts.

10. An endoscope fluid controller according to claim 8, wherein the display section simultaneously indicates the flow rate of each of the various ducts.

11. An endoscope fluid controller comprising:
    a soft duct disposed as part of a fluid duct in an endoscope;
    a regulating valve of a collapse type for changing the collapsing amount of the soft duct; and
    control means for variably controlling the flow rate in the duct by performing the control of the regulating valve;
    wherein a duct deformation preventive member for preventing the deformation of duct shape is disposed at a portion of the soft duct other than the portion where the regulating valve is located;
    wherein a hard covering member for preventing the duct deformation, having an inside diameter slightly larger than an outside diameter of the soft duct, is disposed around the soft duct as the duct deformation preventive member.

12. An endoscope fluid controller comprising:
    a soft duct disposed as part of a fluid duct in an endoscope;
    a regulating valve of a collapse type for changing the collapsing amount of the soft duct; and
    control means for variably controlling the flow rate in the duct by performing the control of the regulating valve;
    wherein a duct deformation preventive member for preventing the deformation of duct shape is disposed at a portion of the soft duct other than the portion where the regulating valve is located;
    wherein an adhesion spring is disposed as a covering member for preventing the duct deformation.

13. An endoscope fluid controller comprising:
    a first control switch disposed in an endoscope operation section;
    control means for controlling fluid in various ducts disposed in an endoscope based on the operation of the first control switch; and
    a second control switch for controlling a fluid by using the control means, which is disposed on a control equipment side to which the endoscope is connected separately from the first control switch,
    wherein a permission switch for making the operation of the second control switch effective is disposed on an endoscope side.

* * * * *